(12) United States Patent
Ihn (10) Patent No.: US 7,891,247 B2
(45) Date of Patent: Feb. 22, 2011

(54) METHOD AND SYSTEM FOR DETECTING AN ANOMALY AND DETERMINING ITS SIZE

(75) Inventor: Jeong-Beom Ihn, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 830 days.

(21) Appl. No.: 11/749,539

(22) Filed: May 16, 2007

(65) Prior Publication Data
US 2008/0283332 A1 Nov. 20, 2008

(51) Int. Cl.
*G01N 9/24* (2006.01)
(52) U.S. Cl. .............................. 73/602; 73/599; 73/620; 73/627
(58) Field of Classification Search .................. 73/602, 73/600, 615, 624, 627, 628, 801; 702/35
See application file for complete search history.

(56) References Cited

U.S. PATENT DOCUMENTS

| 4,187,725 | A |   | 2/1980  | Birjukov et al. |          |
|-----------|---|---|---------|-----------------|----------|
| 4,299,128 | A |   | 11/1981 | Gruber          |          |
| 4,546,652 | A | * | 10/1985 | Virkar et al.   | 73/776   |
| 4,574,637 | A |   | 3/1986  | Adler et al.    |          |
| 4,658,649 | A | * | 4/1987  | Brook           | 73/624   |

(Continued)

FOREIGN PATENT DOCUMENTS

JP 2001215218 8/2001

(Continued)

OTHER PUBLICATIONS

International Search Report, corresponding to International Patent Application No. PCT/US2008/063639, dated Nov. 10, 2008.

(Continued)

*Primary Examiner*—J M Saint Surin
(74) *Attorney, Agent, or Firm*—Charles L. Moore; Moore & Van Allen PLLC (57) ABSTRACT

A method for detecting an anomaly and measuring its size may include generating a wave signal into a structure being evaluated and collecting at least one of any front and back scattered wave data and any side scattered wave data caused by the wave signal impacting an anomaly. The method may also include processing the at least one front and back scattered wave data and side scattered wave data to measure a size, location, and shape of the anomaly.

41 Claims, 5 Drawing Sheets

U.S. PATENT DOCUMENTS

| | | | |
|---|---|---|---|
| 4,817,016 A * | 3/1989 | Thompson et al. | 702/39 |
| 5,184,516 A * | 2/1993 | Blazic et al. | 73/799 |
| 5,760,904 A | 6/1998 | Lorraine et al. | |
| 5,841,031 A | 11/1998 | Chung | |
| 5,987,994 A * | 11/1999 | Maltby et al. | 73/646 |
| 6,128,092 A | 10/2000 | Levesque et al. | |
| 6,311,565 B1 * | 11/2001 | Hinz et al. | 73/801 |
| 6,772,638 B2 * | 8/2004 | Matney et al. | 73/627 |
| 7,024,315 B2 | 4/2006 | Giurgiutiu | |
| 7,231,304 B2 * | 6/2007 | Mitchell | 702/35 |
| 7,263,888 B2 * | 9/2007 | Barshinger et al. | 73/606 |
| 7,333,898 B2 * | 2/2008 | Griess et al. | 702/35 |
| 7,367,236 B2 * | 5/2008 | Georgeson et al. | 73/801 |
| 7,388,365 B2 | 6/2008 | Nokuo et al. | |
| 2004/0206181 A1 | 10/2004 | Coen et al. | |
| 2005/0068041 A1 | 3/2005 | Kress et al. | |
| 2007/0017297 A1 | 1/2007 | Georgeson et al. | |

FOREIGN PATENT DOCUMENTS

| | | |
|---|---|---|
| JP | 2005300274 | 10/2005 |
| WO | 2006009669 | 1/2006 |

OTHER PUBLICATIONS

Written Opinion, corresponding to International Patent Application No. PCT/US2008/063639, dated Nov. 10, 2008.

International Search Report, corresponding to International Patent Application No. PCT/US2009/036188, dated Mar. 22, 2010.

Written Opinion, corresponding to International Patent Application No. PCT/US2009/036188, dated Mar. 22, 2010.

Kress, K-P et al. "Smart Wide-Area Imaging Sensor System (SWISS)." Proceedings of the SPIE—The International Society for Optical Engineering, SPIE, US, vol. 4332, Mar. 5, 2001, pp. 490-496.

* cited by examiner

METHOD AND SYSTEM FOR DETECTING AN ANOMALY AND DETERMINING ITS SIZE

BACKGROUND OF THE INVENTION

The present invention relates to detecting anomalies in a structure, such as an aircraft or other structure, and more particularly to a method and system for detecting an anomaly, such as a delamination or other defect, and estimating or determining its size, shape and location.

New, lightweight composite materials and designs are being used more extensively in the aerospace industry for commercial aircraft and other aerospace vehicles, as well as in other industries. The structures using these composite materials may be formed using multiple plies or layers of material that may be laminated together to form a lightweight, high strength structure. Similar to traditional materials, these structures may be subject to extreme stresses, such as during flight operations for aerospace vehicles or other operations, or damage from an impact or other cause. The multiple plies of material can separate or become delaminated as a result of these stresses or impact. As new and traditional materials are being designed in more optimized manner, there is also the need in the aerospace industry to quickly identify and maintain all structures with better efficiency—improving the dispatch reliability and increasing the in-service use of aircraft and any other similar expensive equipment. As such, there is a need to quantify damage or delamination size in plate-like structures using permanently attached piezoelectric actuators/sensors but such efforts have failed to successfully demonstrate feasibility of actual implementation on real aircraft structures due to heavy dependency on simplified analytical models and lack of simple but robust interpretation techniques relating complex signal responses to damage information and the like. Accordingly, a means to non-destructively inspect for damage and monitor the health or condition of such structures and to determine or measure a size, shape and location of any anomalies or delaminations is needed. Similar needs also exist and similar benefits may be realized for more traditional materials such as metallic structures requiring quick, frequent or infrequent inspections, periodically over time to status the known state of the structures health.

BRIEF SUMMARY OF THE INVENTION

In accordance with an embodiment of the present invention, a method for detecting an anomaly and measuring its size may include generating a wave signal into a structure being evaluated and collecting at least one of any front and back scattered wave data and any side scattered wave data caused by the wave signal impacting an anomaly. The method may also include processing the at least one front and back scattered wave data and side scattered wave data to measure a size, location, and shape of the anomaly.

In accordance with another embodiment of the present, a method of detecting an anomaly and measuring its size may include generating baseline wave data for a structure. The method may also include generating a wave into the structure being evaluated and collecting at least one of any front and back scattered wave data and any side scattered wave data caused by energy of the wave being at least partially reflected by an anomaly. The method may further include measuring a size of the anomaly from the at least one of front and back scattered wave data and side scattered wave data.

In accordance with another embodiment of the present invention, a system for detecting an anomaly and measuring its size may include an actuator for generating and introducing a wave signal into a structure being evaluated. The system may also include a sensor for collecting at least one of any front and back scattered wave data and any side scattered wave data caused by energy of the wave signal being at least partially reflected by an anomaly. The system may further include hardware, such as a structural health management unit for processing the at least one of any front and back scattered wave data and any side scattered wave data to measure a size of the anomaly.

Other aspects and features of the present invention, as defined solely by the claims, will become apparent to those ordinarily skilled in the art upon review of the following non-limited detailed description of the invention in conjunction with the accompanying figures.

DETAILED DESCRIPTION OF THE INVENTION

The following detailed description of embodiments refers to the accompanying drawings, which illustrate specific embodiments of the invention. Other embodiments having different structures and operations do not depart from the scope of the present invention.

Figure 1:
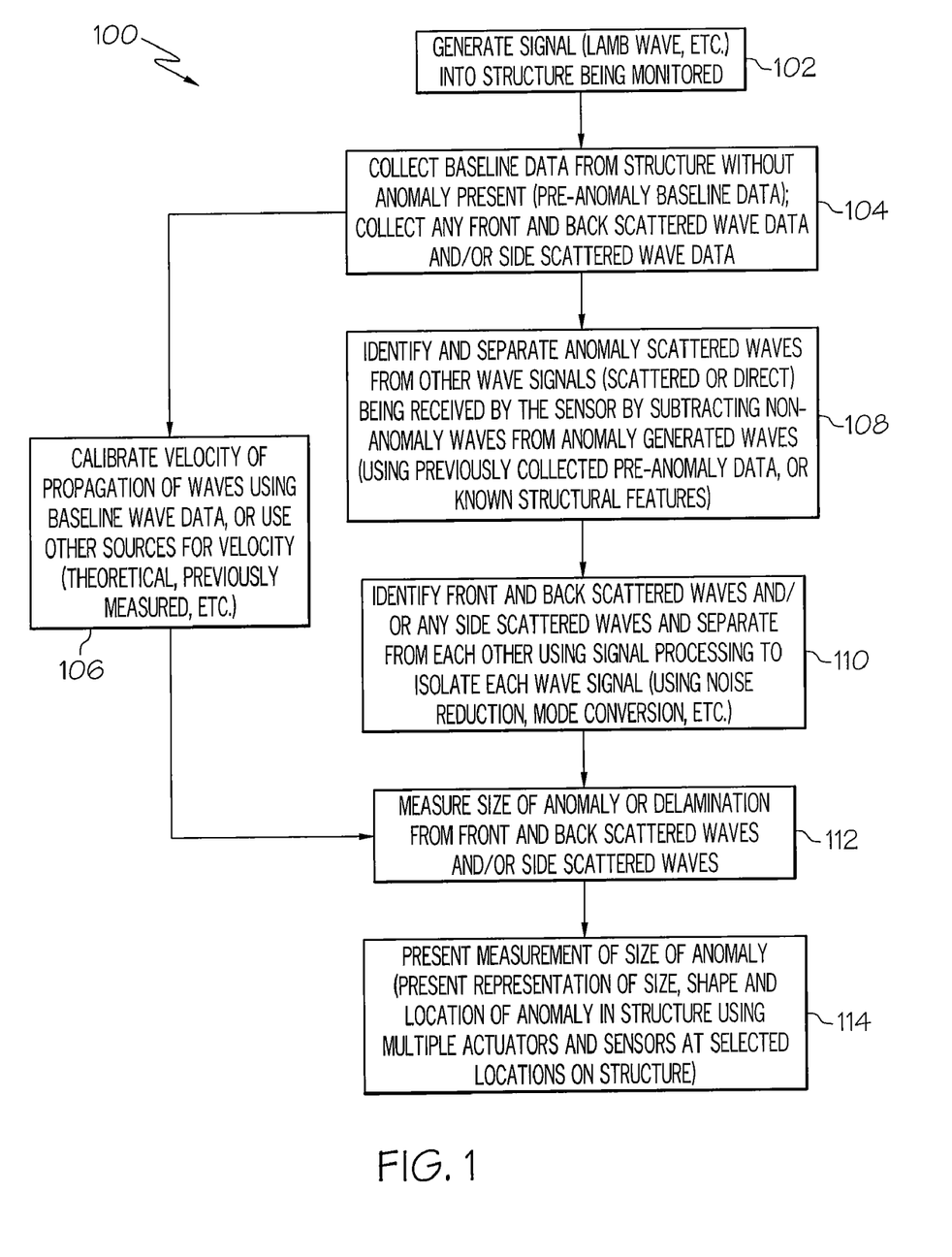
FIG. 1 is a flow chart of an example of a method for detecting and determining the size of an anomaly in a structure in accordance with an embodiment of the present invention.

FIG. 1 is a flow chart of an example of a method 100 for detecting and determining the size of an anomaly in a structure in accordance with an embodiment of the present invention. In block 102, a signal, pulse wave, lamb wave or similar wave signal may be generated and directed into a structure being monitored.

Figure 2:
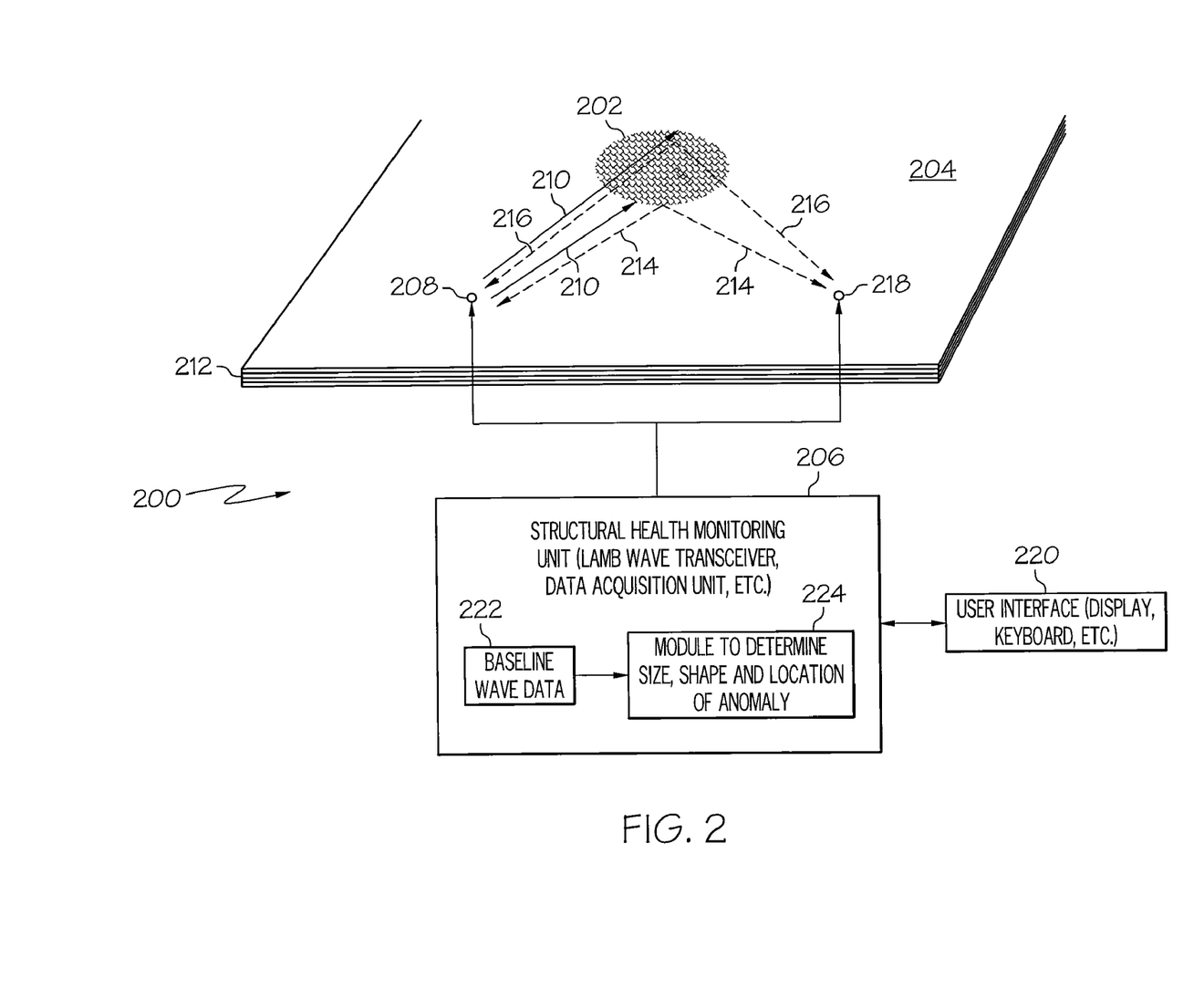
FIG. 2 is a block diagram of an exemplary system for detecting and determining the size of an anomaly in a structure in accordance with an embodiment of the present invention.

Referring also to FIG. 2, FIG. 2 is a block diagram of an exemplary system 200 for detecting and determining the size of an anomaly 202 in a structure 204 in accordance with an embodiment of the present invention. A structural health monitoring unit 206 may be used to generate the signal, pulse wave, or other wave signal, and an actuator or combination actuator and sensor 208 may generate, transfer or direct the wave signal, illustrated by arrow 210 in FIG. 2, into the structure 204 or object being monitored. The structural health monitoring unit 206 may be a lamb wave generator or transceiver, data acquisition unit capable of transmitting and receiving signals for structural health monitoring as described herein or the like.

The actuator or combination actuator-sensor 208 may be an electromechanical actuator/sensor capable of generating or directing a signal for structural health monitoring, such as a lamb wave or similar signal or wave, into the structure 204. An example of the actuator or combination actuator-sensor 208 may be a piezoelectric actuator/sensor or similar device attachable to the structure 204.

The structure 204 or object may be formed by a plurality 212 of plies or layers of composite material, a solid metallic material, or other similar solid or laminated material. The structure 204 or object may be a vehicle, such as an aerospace vehicle, terrestrial vehicle, watercraft, civil structure, such as a bridge, building or other structure, or any object were monitoring the structural health or condition is desired.

Referring back to FIG. 1, in block 104, any front and back scattered wave data caused by the wave signal 210 impacting an anomaly, such as anomaly 202, crack or delamination in the example of FIG. 2, may be collected. The front and back scattered waves or wave data are illustrated in FIG. 2 by broken or dashed arrows 214 and 216, respectively. The front and back scattered wave data 214 and 216 or signal may be collected by the combination actuator-sensor 208 if the actuator-sensor 208 is self-sensing. The front and back scattered wave data 214 and 216 or signal may also be collected by a sensor 218 capable of receiving such wave data or pulses and transmitting the received or collected wave data to the structural health monitoring unit 206 for analysis to measure the size of the anomaly 202 or delamination. The sensor 218 may also be an electromechanical device, such as a piezoelectric sensor or similar device capable of sensing the front and back scattered waves 214 and 216. In another embodiment of the present invention, side scattered waves or wave data may be collected or may be collected in addition to the back and front scatter waves. An example of collecting side scattered waves will be described with reference to FIG. 5.

The system 200 may include actuators 208 without a sensing capability and sensors 218 in what may be referred to as a pitch-catch arrangement or pitch-catch actuators/sensors and may operate in a pitch-catch mode. The actuators 208 may transmit or pitch wave signals 210 into the structure 204 and the sensors 218 may receive or catch any front and back scattered wave data 214 and 216 from any anomaly 202. Alternatively, as described above, the devices 208 and 218 may both be combination actuator and sensor devices for both transmitting the wave signal 210 and receiving the front and back scattered wave data 214 and 216 and sending the data to the structural health monitoring unit 206 to determine or measure the size of the anomaly 202. The arrangement may be referred to as a pulse-echo arrangement or pulse-echo actuators/sensors and may operate in a pulse-echo mode. Any combination of multiple pitch-catch actuators/sensors or pulse-echo actuators/sensors that may be positioned at predetermined locations to measure the size and location of the anomaly 202. The combination actuator and sensor devices may also operate in a pitch-catch mode.

In accordance with another embodiment of the present invention, a plurality of actuators or combination actuator-sensors, similar to actuator/sensor 208, and a plurality of sensors, similar to sensor 218, may be positioned at selected locations on the structure 204 relative to one another to measure the size, shape and location of any anomaly or delamination in the structure 204.

Also in block 104 of FIG. 1, baseline wave data for the structure 204 may also be collected. The baseline wave data may be collected (a) before the structure 204 or object is placed in service, (b) at some point in time before beginning a structural health monitoring program on the structure 204, or (c) anytime during the monitoring process before the damage anomaly is created.

Figure 3:
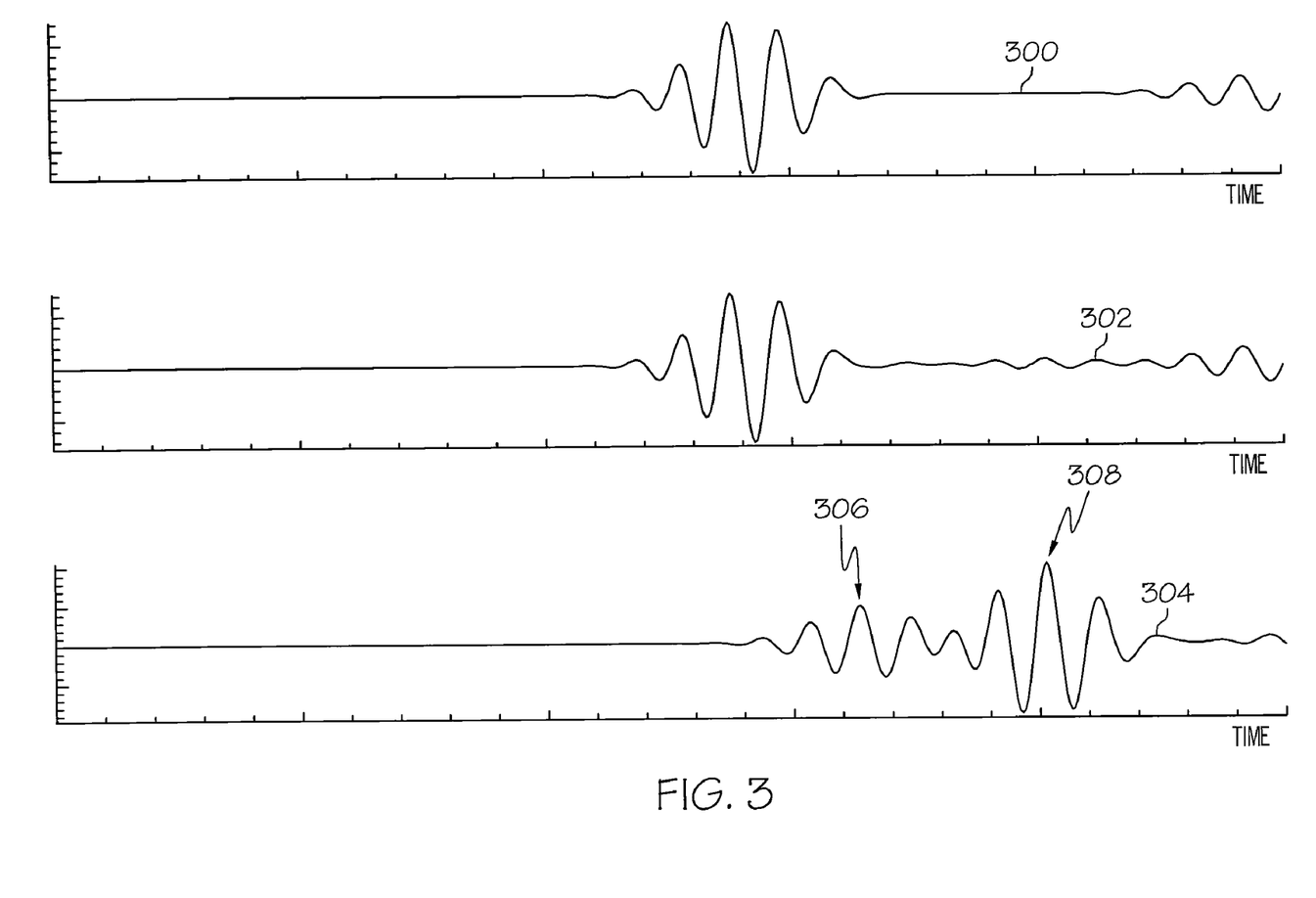
FIG. 3 is an illustration of waveforms for detecting and determining the size of an anomaly in a structure in accordance with an embodiment of the present invention.

In block 106, a velocity of propagation of waves or signals in the structure 204 may be calibrated using the baseline wave data or other sources for velocity, such as theoretical velocity in the particular structure, previously measured velocity in the structure 204 or similar structures or other sources for velocity. The calibrated velocity of propagation of the waves may be used in measuring the size of any anomaly or delamination from the front and back scattered wave data 214 and 216 as described herein. An example of a baseline waveform 300 is illustrated in FIG. 3. FIG. 3 also illustrates an example of a waveform 302 illustrating detection of an anomaly and a waveform 304 illustrating front scattered wave data 306 and back scattered wave data 308.

In block 108, signal processing may be performed on the front and back scattered wave data 214 and 216 using the collected baseline wave data for the structure 204. The scattered waves 214 and 216 induced by the anomaly 202 can be decoupled or separated from any other waves, such as directly transmitted waves from the actuator 208 to sensor 218 and/or other possible reflected waves from any structural boundaries present in the structure 204, by subtracting other reflected waves that are not being reflected from the anomaly 202. One method to do this is by subtracting post damage data from pristine (baseline) wave data.

In block 110, the front and back scattered waves 214 and 216 (and/or side scattered wave waves in other embodiments of the present invention) may be separated or separately identified. The front and back scattered waves 214 and 216 may be separated or identified using signal processing to isolate each wave signal. Examples of signal processing techniques that may be used may include mode decomposition or mode conversion, noise cancellation or reduction or other known signal processing techniques. Applying mode decomposition to the reflected wave signals will help decompose the combined scatter wave which consists of both front scatter and back scatter into individual components that can then be identified into front scatter and back scatter components and the individual time of flight for each wave and be uniquely measured. Other signal processing techniques such as noise cancellation can also be used to more clearly identify the true front scatter and back scatter waves signals.

In block 112, the size of the delamination or other anomaly may be measured from the front and back scattered wave data 214 and 216 (and/or side scattered wave data in other embodiments of the present invention). In an embodiment of the present invention, the size of the delamination or anomaly may be measured based on a difference in arrival time of the front and back scattered wave data 214 and 216 at the sensors 208 and 218 or a Time-of-Flight (TOF) of the wave and based on a calibrated velocity of the wave propagation (V) in the structure 204. The TOF may be defined as the time from when a signal or wave is transmitted and the front and back scattered waves are respectively received. Examples of measuring damage size for different actuator/sensor configurations based on the measured Time-of-Flight information of the back scattered wave ($TOF_b$), the measured Time-of-Flight information of the front scattered ($TOF_f$) and the calibrated velocity V within the structure will be described with reference to FIGS. 4-6.

In block 114, the measurement of the size of the delamination or other anomaly may be presented to a user. The size of the delamination or other anomaly may be presented on a user interface 220 (FIG. 2), such as a display. The user interface 220 may also include a keyboard, computer pointing device or other means for interfacing with and controlling operation of the structural health monitoring unit 206.

Also in block 114, in another embodiment of the present invention, a representation of the measured size, shape, and location of the delamination or other anomaly may be presented. Similar to that previously describe, multiple actuators and sensors may be attached or mounted to a structure at selected locations on the structure. The multiple actuators may send wave signals into the structure. The sensors may receive front and back scattered wave data from any anomaly in the structure to measure and present the representation of the measured size, shape and location of the anomaly. An example of a configuration operable in either a pitch-catch mode or a pulse-echo mode for detecting any anomaly and measuring the anomaly's size and shape will be described with reference to FIGS. 7A and 7B.

Referring again to FIG. 2, the structural health monitoring unit 206 may include a data storage element 222 to store the baseline wave data and any other data for analyzing the front and back scatter wave data 214 and 216. The structural health monitoring unit 206 may also include a module 224 to determine the size of the anomaly 202 or delamination. In another embodiment of the present invention the module 224 may be adapted to determine the size, shape and location of the anomaly if multiple actuators and sensors are used similar to that previously described. The elements of the method 100 may be embodied in the module 224.

Figure 4:
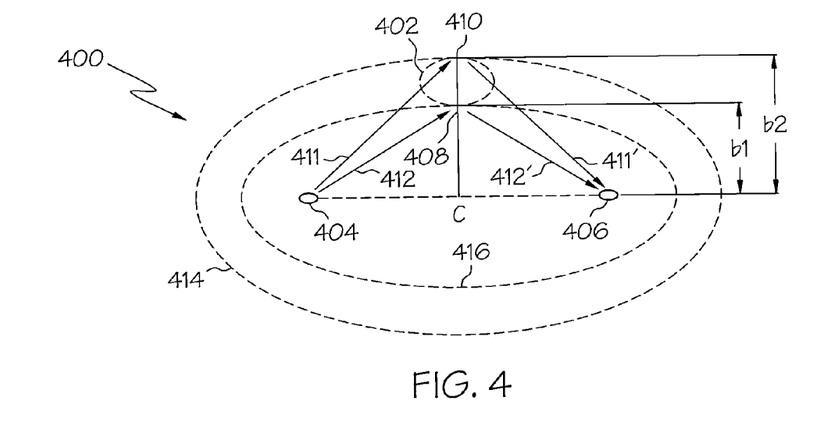
FIG. 4 illustrates an example of a pitch-catch actuator-sensor configuration for detecting and determining the size of any anomaly in a structure when the anomaly is not in a direct path between an actuator and a sensor in accordance with an embodiment of the present invention.

FIG. 4 illustrates an example of a pitch-catch actuator-sensor configuration 400 for detecting any anomaly 402 or damage in a structure and determining the size of the anomaly 402 when the anomaly 402 is not in a direct path between an actuator 404 and a sensor 406 in accordance with an embodiment of the present invention. The size of the anomaly or damage may be determined by equation 1:

$$D = b_2 - b_1 = \sqrt{\left(\frac{1}{2}TOF_b \cdot V\right)^2 - \left(\frac{c}{2}\right)^2} - \sqrt{\left(\frac{1}{2}TOF_f \cdot V\right)^2 - \left(\frac{c}{2}\right)^2} \quad \text{Eq. 1}$$

In equation 1, D is the distance between the front boundary 408 and the back boundary 410 of the anomaly as represented by the difference between b1 and b2, the respective distances from the actuator 404 and sensor 406 and the front and back boundaries 408 and 410 or edges of the anomaly 402. $TOF_b$ is the Time-of-Flight of a wave signal represented by arrow 411 in FIG. 4 from the actuator 404 to the sensor 406 scattered from the back boundary 410 of the anomaly 402 as represented by arrow 411'. $TOF_f$ is the Time-of-Flight of the wave signal represent by arrow 412 from the actuator 404 to the sensor 406 scattered from the front boundary 408 of the anomaly as represented by arrow 412'. V is the velocity of the wave signal propagating through the material and may be the calibrated velocity of the wave or signal in the particular material or structure. Equation 1 assumes an isotropic structure or material and therefore V is constant. The V may be described as being an angle dependent variable in the case of an anisotropic structure. Accordingly, V may vary with angle of the actuator 404 and sensor 406 relative to the anomaly 402 in an anisotropic structure. Module 224 in FIG. 2 may be adapted or modified to compensate for the structure under evaluation being anisotropic. In equation 1, the variable c represents the distance between the actuator 404 and sensor 406.

The substantially elliptically shaped broken or dashed lines 414 and 416 illustrate boundaries of an area associated the actuator 404 and sensor 406 within which any anomaly or damage may be detected and its size determined by the actuator 404 and sensor 406 operating in the pitch-catch mode, as described above, wherein the actuator 404 generates a wave or signal and the sensor 406 senses any of the wave signal scattered by the boundaries of the anomaly 402 or delamination.

Figure 5:
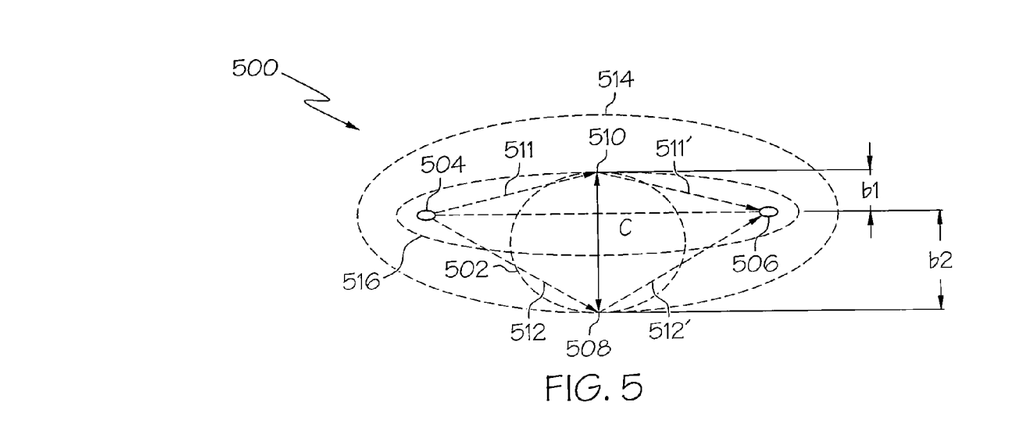
FIG. 5 illustrates an example of a pitch-catch actuator-sensor configuration for detecting and determining the size of any anomaly in a structure when the anomaly is on a direct path between an actuator and a sensor in accordance with an embodiment of the present invention.

FIG. 5 illustrates an example of a pitch-catch actuator-sensor configuration 500 for detecting and determining the size of any anomaly 502 in a structure when the anomaly 502 is on a direct path between an actuator 504 and a sensor 506 in accordance with an embodiment of the present invention. The size of the anomaly 502 or damage may be determined by equation 2:

$$D = b_2 + b_1 = \sqrt{\left(\frac{1}{2}TOF_b \cdot V\right)^2 - \left(\frac{c}{2}\right)^2} + \sqrt{\left(\frac{1}{2}TOF_f \cdot V\right)^2 - \left(\frac{c}{2}\right)^2} \quad \text{Eq. 2}$$

The elements of equation 2 are the same as those described with respect to equation 1 above. Equation 2 assumes the structure is isotropic and therefore V will be constant. The velocity V may vary with an angle of the anomaly 502 relative to the actuator 504 and sensor 506 in anisotropic structures.

The broken or dashed lines 514 and 516 illustrate boundaries of an area associated the actuator 504 and sensor 506 where any anomaly or damage may be detected and its size measured by the actuator 504 and sensor 506 operating in the pitch-catch mode similar to that previously described. The paths 511 and 512 represent a signal being sent from the actuator 504. The paths 511' and 512' represent the signal being scattered from respective sides 510 and 508 of the anomaly 502, and being received at the sensor 506. In this scenario, the scatter of primary interest is scattered from the sides 508 and 510 of the anomaly 502.

Figure 6:
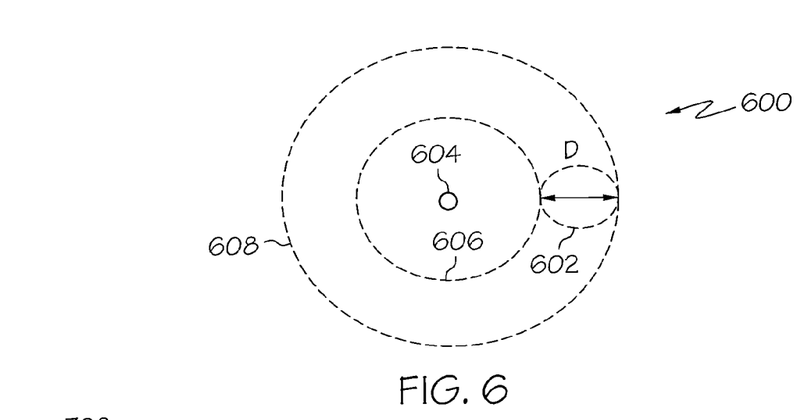
FIG. 6 illustrates an example of a pitch-catch actuator-sensor configuration for detecting and determining the size of any anomaly in a structure when the anomaly is on a direct path between an actuator and a sensor in accordance with an embodiment of the present invention.

FIG. 6 illustrates an example of a pulse-echo (self-sensing) configuration 600 for detecting and measuring the size any anomaly 602 in a structure in accordance with an embodiment of the present invention. At least one device 604 or combination actuator-sensor device that is capable of both generating a wave signal and receiving back scattered wave data may be provided. The size of the anomaly 602 may be determined by equation 3:

$$D = \frac{1}{2}(TOF_b - TOF_f) \cdot Vg \quad \text{Eq. 3}$$

The elements of equation 3 may be the same as those in Equations 1 and 2. The velocity V may vary with an angle relative to the device 604 and the anomaly 602 in an anisotropic structure. The broken or dashed lines 606 and 608 illustrate boundaries of areas associated the device 604 where any anomaly or damage may be detected and its size measured by the device 604 operating in the pulse-echo mode.

Figure 7A:
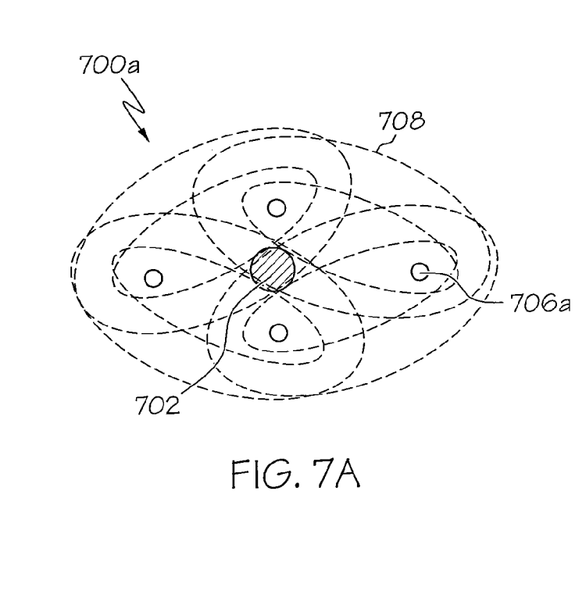
FIGS. 7A and 7B illustrate an example of a sensor-actuator configuration operable in either a pitch-catch mode (FIG. 7A) or a pulse-echo mode (FIG. 7B) for detecting any anomaly and determining the anomaly's size and shape in accordance with an embodiment of the present invention.
Figure 7B:
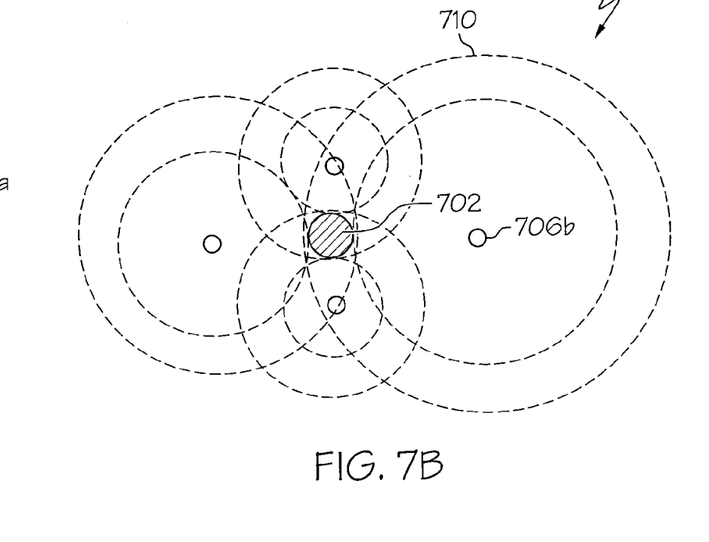

FIGS. 7A and 7B illustrate an example of a configuration 700a and 700b operable in either a pitch-catch mode (FIG. 7A) or a pulse-echo mode (FIG. 7B) for detecting any anomaly 702 and determining or measuring the anomaly's size and shape in accordance with an embodiment of the present invention. The configuration 700 may include multiple devices 706 or combination actuators/sensors capable of both generating a signal or wave and receiving front and back scattered waves or data from any anomaly 702. The devices 706 may also be separate actuators for generating a signal or wave and sensors for receiving the front and back scattered wave data. The devices 706 or separate actuators and sensors may be positioned at predetermined locations on an object to be tested or evaluated.

In FIG. 7A the devices 706a may be operated in a pitch-catch mode or configuration similar to that previously described. In the pitch-catch mode, selected devices 706a may generate or pitch a wave signal and other devices 706a may receive or catch any front and back scattered waves or data from any anomaly 702 or damage. The substantially elliptically shaped broken or dashed lines 708 in FIG. 7A illustrate boundaries of areas associated with each device 706a where any anomaly or damage may be detected and its size determined by the respective device 706a in the configuration 700a operating in the pitch-catch mode.

In FIG. 7B, the devices 706b may be operated in a pulse-echo mode or configuration similar to that previously described. In the pulse-echo mode, each device 706b may generate or pulse a wave or signal and the same device 706b may also receive any front and back scattered waves or data from any anomaly 702. The substantially circular broken or dashed lines 710 associated with each device 706b in FIG. 7B illustrate boundaries of areas where any anomaly or damage may be detected by the respective devices 706b in the configuration 700b operating in the pulse-echo mode. Damage volume may also be determined when multiple devices 706 or actuator-sensors are used by utilizing multiple scattered wave data and scatter imaging techniques.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," and "includes" and/or "including" when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the invention has other applications in other environments. This application is intended to cover any adaptations or variations of the present invention. The following claims are in no way intended to limit the scope of the invention to the specific embodiments described herein.

What is claimed is:

1. A method for detecting an anomaly and measuring its size, comprising:

generating a lamb wave signal into a structure being evaluated;

collecting both front and back scattered wave data caused by the generated lamb wave signal impacting an anomaly, wherein the front scattered wave data is wave data scattered by a front edge of the anomaly relative to a device generating the lamb wave signal and the back scattered wave data is wave data scattered by the lamb wave passing through the anomaly and being scattered by a back edge of the anomaly relative to the device generating the lamb wave signal; and processing the front and back scattered wave data to measure a size of the anomaly.

2. The method of claim 1, further comprising generating baseline wave data for the structure.

3. The method of claim 2, further comprising calibrating a velocity of propagation of waves in the structure by using the baseline wave data.

4. The method of claim 2, further comprising performing signal processing on the front and back scattered wave data using the baseline wave data for the structure.

5. The method of claim 1, further comprising:

identifying the front and back scattered wave data; and separating anomaly scattered wave signals from any other wave signals.

6. The method of claim 5, wherein separating the anomaly scattered wave signals from any other wave signals comprises subtracting any other wave signals from the anomaly scattered wave signals using data collected before any anomaly or using known structural features of the structure.

7. The method of claim 5, further comprising using signal processing to isolate each wave signal.

8. The method of claim 5, further comprising using at least one of mode conversion and noise conversion to identify the of front and back scattered waves and to separate each signal.

9. The method of claim 1, further comprising presenting the measurement of the size of the anomaly.

10. The method of claim 1, further comprising presenting a representation of the measured size of the anomaly and an estimated shape of the anomaly and location of the anomaly in the structure.

11. The method of claim 1, further comprising positioning a multiplicity of actuators for generating a wave signal and a multiplicity of sensors for collecting the front and back scattered wave data at selected locations on the structure relative to one another to determine the size, shape and location of the anomaly or other anomalies.

12. The method of claim 11, wherein at least some of the multiplicity of actuators and sensors may be combination actuator/sensors for self sensing.

13. The method of claim 1, wherein the structure is one of an aircraft, a terrestrial vehicle, a watercraft, and a civil structure.

14. The method of claim 1, wherein the anomaly comprises a delamination in a material used to form the structure.

15. The method of claim 1, further comprising measuring the size of the anomaly based on a difference in arrival time of the front and back scattered wave data at a sensor and based on a calibrated velocity of wave propagation in the structure.

16. The method of claim 1, further comprising measuring the size of the anomaly based on a time-of-flight of the front and back scattered wave data and a calibrated velocity of wave propagation in the structure.

17. The method of claim 16, wherein the calibrated velocity comprises a varying calibrated velocity of wave propagation in response to the structure being anisotropic.

18. The method of claim 1, further comprising operating in one of a pitch-catch mode and a pulse-echo mode to detect the anomaly and measure its size.

19. The method of claim 1, further comprising collecting any side scattered wave data caused by the generated wave signal impacting the anomaly.

20. A method of detecting an anomaly and measuring its size, comprising:
   generating baseline wave data for a structure;
   generating a lamb wave into the structure being evaluated;
   collecting both front and back scattered wave data caused by energy of the lamb wave being at least partially reflected or scattered by an anomaly, wherein the front scattered wave data is wave data scattered by a front edge of the anomaly relative to a device generating the lamb wave signal and the back scattered wave data is wave data scattered by the lamb wave passing through the anomaly and being scattered by a back edge of the anomaly relative to the device generating the lamb wave signal; and
   measuring a size of the anomaly from the front and back scattered wave data.

21. The method of claim 20, further comprising identifying and separating anomaly scattered wave signals from any other wave signals.

22. The method of claim 21, further comprising subtracting any other wave signals from the anomaly scattered wave signals using data collected before any anomaly or using known structural features of the structure.

23. The method of claim 21, further comprising using signal processing to isolate each wave signal.

24. The method of claim 21, further comprising using at least one of mode decomposition and noise cancellation to separate each of the front and back scattered wave signals.

25. The method of claim 20, further comprising:
   determining a velocity of propagation of waves in the structure;
   calibrating the velocity of waves in the structure; and
   measuring the size of the anomaly from a time-of-flight of the front and back scattered waves based on the calibrated velocity of propagation of waves in the structure.

26. The method of claim 25, wherein the calibrated velocity comprises a varying calibrated velocity relative to an angle of wave propagation in response to the structure being anisotropic.

27. The method of claim 20, further comprising operating in one of a pitch-catch mode and a pulse-echo mode.

28. The method of claim 20, further comprising arranging a plurality of devices for generating the wave and collecting the front and back scattered wave data in one of a pitch-catch configuration and a pulse-echo configuration.

29. A system for detecting an anomaly and measuring its size, comprising:
   an actuator for generating a lamb wave signal into a structure being evaluated;
   a sensor for collecting both front and back scattered wave data or signals caused by energy of the lamb wave signal being at least partially reflected or scattered by an anomaly, wherein the front scattered wave data or signals are wave data or signals scattered by a front edge of the anomaly relative to the actuator and the back scattered wave data or signals are wave data or signals scattered by the lamb wave passing through the anomaly and being scattered by a back edge of the anomaly relative to the actuator; and
   a structural health monitoring unit for processing the front and back scattered wave data or signals to measure a size of the anomaly.

30. The system of claim 29, further comprising a module to identify and separate anomaly scattered wave signals from any other wave signals.

31. The system of claim 30, wherein the module is adapted to use signal processing to isolate each wave signal.

32. The system of claim 29, further comprising a module to separate each of the of front and back scattered wave signals.

33. The system of claim 32, further comprising a database for storing baseline wave data for the structure.

34. The system of claim 33, further comprising a module to calibrate a velocity of propagation of waves in the structure using the baseline wave data for the structure.

35. The system of claim 34, further comprising a module to measure the size of the anomaly from a time-of-flight of the front and back scattered waves based on the calibrated velocity of propagation of waves in the structure.

36. The system of claim 29, wherein the structural health monitoring unit comprises an ultrasonic wave generator.

37. The system of claim 29, wherein the actuator comprises a combination actuator/sensor capable of self-sensing the front and back scattered wave data.

38. The system of claim 37, further comprising a plurality of actuators and sensors or combination actuator/sensors positionable at selected locations on the structure relative to one another to measure, size, shape and location of the anomaly or other anomalies.

39. A system for detecting an anomaly and measuring its size, comprising:
   a device for generating a lamb wave signal into a structure being evaluated and for collecting both front and back scattered wave data caused by energy of the wave signal being at least partially reflected or scattered by an anomaly, wherein the front scattered wave data is wave data scattered by a front edge of the anomaly relative to the device generating the lamb wave signal and the back scattered wave data is wave data scattered by the lamb wave passing through the anomaly and being scattered a back edge of the anomaly relative to the device generating the lamb wave signal; and
   a structural health monitoring unit for processing the at least one of any front and back scattered wave data and side scattered wave data to measure a size of the anomaly.

40. The system of claim 39, further comprising a plurality of devices for generating the wave signal and collecting the front and back scattered wave data, wherein the plurality of devices are configured for operation in one a pulse-echo mode and a pitch-catch mode.

41. The system of claim 39, further comprising a module for compensating for the structure being anisotropic by setting the velocity value based on an orientation angle of the wave signal.

* * * * *